United States Patent
Bauduin et al.

(10) Patent No.: US 9,532,906 B2
(45) Date of Patent: Jan. 3, 2017

(54) ABSORBENT ARTICLE AND PROCESS FOR MAKING IT

(71) Applicants: BOSTIK INC., Wauwatosa, WI (US); BASF SE, Ludwigshafen (DE)

(72) Inventors: Christophe Bauduin, Plankstadt (DE); Jean-Francois Chartrel, Cuts (FR); Thomas Daniel, Waldsee (DE); Julien Liger, Margny les Compiegnes (FR); Renate Wuestefeld, Speyer (DE)

(73) Assignees: BASF SE, Ludwigshafen (DE); BOSTIK INC., Wauwatosa, WI (US)

( * ) Notice: Subject to any disclaimer, the term of this patent is extended or adjusted under 35 U.S.C. 154(b) by 0 days.

(21) Appl. No.: 14/353,342

(22) PCT Filed: Oct. 24, 2012

(86) PCT No.: PCT/EP2012/071070
§ 371 (c)(1),
(2) Date: Apr. 22, 2014

(87) PCT Pub. No.: WO2013/060732
PCT Pub. Date: May 2, 2013

(65) Prior Publication Data
US 2014/0276511 A1   Sep. 18, 2014

Related U.S. Application Data

(60) Provisional application No. 61/582,023, filed on Dec. 30, 2011, provisional application No. 61/582,047, filed on Dec. 30, 2011.

(30) Foreign Application Priority Data

Oct. 24, 2011 (EP) .................................. 11186336
Oct. 24, 2011 (EP) .................................. 11186337

(51) Int. Cl.
*A61F 13/15* (2006.01)
*A61F 13/539* (2006.01)
(Continued)

(52) U.S. Cl.
CPC ... *A61F 13/15699* (2013.01); *A61F 13/15658* (2013.01); *A61F 13/15707* (2013.01);
(Continued)

(58) Field of Classification Search
CPC .................. A61F 13/5323; A61F 2013/00748; A61F 13/0209; A61F 13/0213; A61F 2013/428; A61F 2013/5307; A61F 2013/00229; A61F 2013/00523; A61F 2013/00727; A61F 2013/00753; A61F 2013/530306; B23B 2553/00; B23B 2553/02; B23B 2253/026; B23B 2555/00
See application file for complete search history.

(56) References Cited

U.S. PATENT DOCUMENTS 3,881,491 A * 5/1975 Whyte .......................... 604/370
4,068,618 A   1/1978 Greenberg
(Continued)

FOREIGN PATENT DOCUMENTS

| EP | 1621166 A1 | 2/2006 |
|---|---|---|
| EP | 2444044 A1 | 4/2012 |
| WO | 95/21596 A1 | 8/1995 |

OTHER PUBLICATIONS

International Search Report from PCT/EP2012/071070 dated Nov. 29, 2012.
(Continued)

*Primary Examiner* — Adam Marcetich
(74) *Attorney, Agent, or Firm* — Millen, White, Zelano & Branigan, P.C.

(57) ABSTRACT

The present invention is directed to a liquid-absorbing article comprising:
  a first sheet layer presenting an array of absorbent receiving pockets;
(Continued)

masses of superabsorbent material, which masses are placed in said absorbent receiving pockets;

a second sheet layer placed on top of the first layer;

bonding beads placed between the respective pockets.

19 Claims, 5 Drawing Sheets

(51) Int. Cl.
- *A61F 13/53* (2006.01)
- *A61F 13/538* (2006.01)
- *A61F 13/532* (2006.01)

(52) U.S. Cl.
CPC ...... *A61F 13/15747* (2013.01); *A61F 13/538* (2013.01); *A61F 13/539* (2013.01); *A61F 13/5323* (2013.01); *A61F 13/532* (2013.01); *A61F 2013/5395* (2013.01); *A61F 2013/530481* (2013.01); *A61F 2013/530547* (2013.01); *A61F 2013/530562* (2013.01); *A61F 2013/53908* (2013.01); *A61F 2013/53925* (2013.01); *A61F 2013/53933* (2013.01); *A61F 2013/53958* (2013.01); *Y10T 156/10* (2015.01); *Y10T 156/1049* (2015.01)

(56) References Cited

U.S. PATENT DOCUMENTS

| | | | |
|---|---|---|---|
| 4,260,443 A * | 4/1981 | Lindsay | A61F 13/15699 156/220 |
| 4,274,577 A * | 6/1981 | Walsh, Jr. | 229/67.3 |
| 4,381,783 A | 5/1983 | Elias | |
| 4,675,216 A | 6/1987 | DuForest et al. | |
| 4,892,535 A | 1/1990 | Bjornberg et al. | |
| 5,376,198 A * | 12/1994 | Fahrenkrug et al. | 156/164 |
| 5,425,725 A | 6/1995 | Tanzer et al. | |
| 5,429,788 A | 7/1995 | Ribble et al. | |
| 5,433,715 A | 7/1995 | Tanzer et al. | |
| 5,494,622 A | 2/1996 | Heath et al. | |
| 5,865,824 A | 2/1999 | Chen et al. | |
| 5,964,743 A * | 10/1999 | Abuto et al. | 604/385.01 |
| 6,129,717 A | 10/2000 | Fujioka et al. | |
| 6,139,912 A | 10/2000 | Onuschak et al. | |
| 7,744,713 B2 | 6/2010 | Blessing et al. | |
| 7,838,722 B2 | 11/2010 | Blessing et al. | |
| 8,268,424 B1 | 9/2012 | Suzuki et al. | |
| 2003/0119412 A1 * | 6/2003 | Sayovitz et al. | 442/409 |
| 2004/0243081 A1 * | 12/2004 | Suzuki | A61F 13/49426 604/378 |
| 2005/0027277 A1 * | 2/2005 | Mizutani et al. | 604/385.101 |
| 2006/0021695 A1 | 2/2006 | Blessing et al. | |
| 2006/0024433 A1 | 2/2006 | Blessing et al. | |
| 2006/0198997 A1 * | 9/2006 | Goossens et al. | 428/304.4 |
| 2006/0202379 A1 | 9/2006 | Bentley et al. | |
| 2006/0206073 A1 * | 9/2006 | Crane et al. | 604/378 |
| 2007/0250026 A1 * | 10/2007 | Venturino et al. | 604/385.01 |
| 2008/0312617 A1 | 12/2008 | Hundorf et al. | |
| 2009/0030155 A1 | 1/2009 | Daniel et al. | |
| 2009/0326495 A1 * | 12/2009 | MacDonald | A61F 13/495 604/367 |
| 2010/0062165 A1 | 3/2010 | Suzuki et al. | |
| 2010/0062934 A1 | 3/2010 | Suzuki et al. | |
| 2010/0063470 A1 | 3/2010 | Suzuki et al. | |
| 2010/0100065 A1 * | 4/2010 | Bianco et al. | 604/367 |
| 2010/0318049 A1 * | 12/2010 | Meyer | A61F 13/53 604/366 |
| 2011/0017398 A1 | 1/2011 | Blessing et al. | |
| 2011/0041999 A1 | 2/2011 | Hundorf et al. | |
| 2011/0166540 A1 * | 7/2011 | Yang | A61F 13/15203 604/367 |
| 2014/0261987 A1 * | 9/2014 | Chartrel | 156/199 |

OTHER PUBLICATIONS

International Search Report from PCT/EP2012/071071 dated Nov. 29, 2012.

International Search Report from PCT/EP2012/071072 dated Nov. 29, 2012.

International Search Report from PCT/EP2012/071073 dated Nov. 28, 2012.

Related U.S. Appl. No. 14/353,317, filed Apr. 22, 2014.

Related U.S. Appl. No. 14/353,318, filed Apr. 22, 2014.

Related U.S. Appl. No. 14/353,320, filed Apr. 22, 2014.

\* cited by examiner

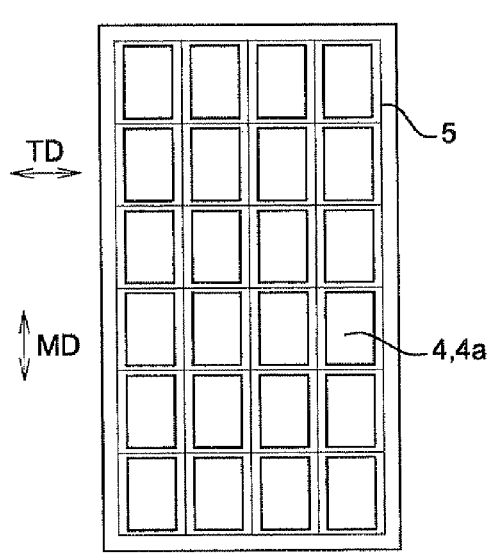
FIG. 1B
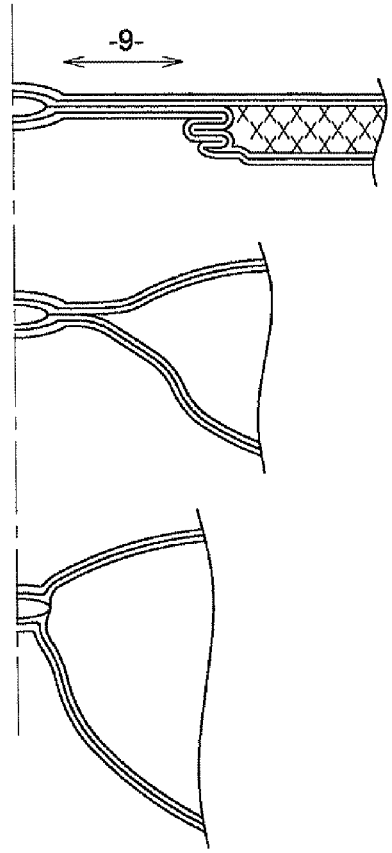
FIG. 2A
FIG. 2B
FIG. 2C
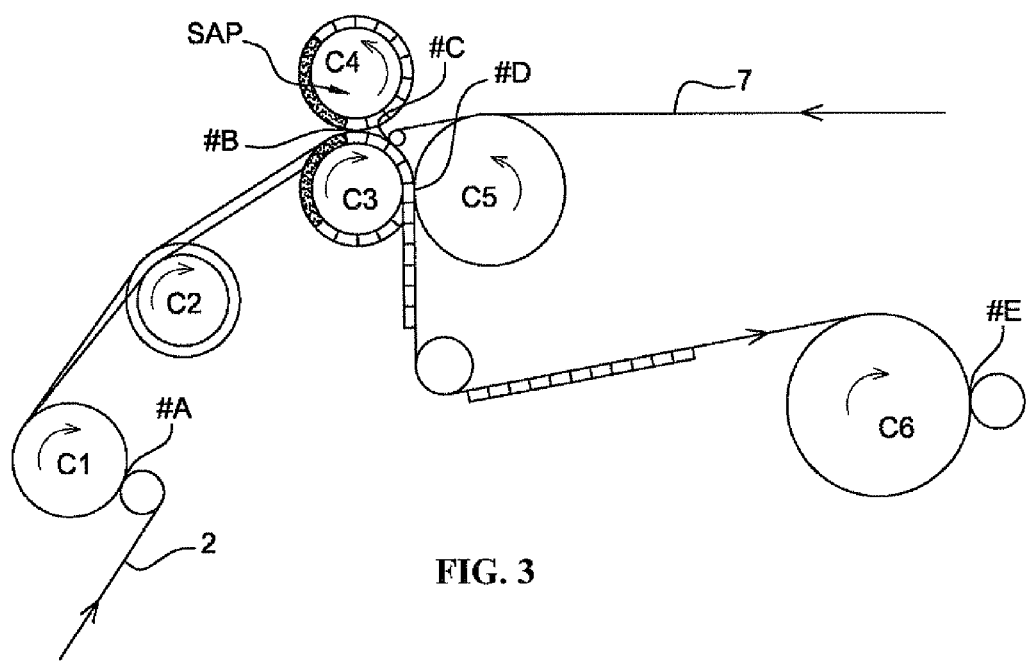
FIG. 3

ABSORBENT ARTICLE AND PROCESS FOR MAKING IT

RELATED APPLICATIONS

The present application claims priority from EP11186336 filed Oct. 24, 2011, from EP11186337 filed Oct. 24, 2011, U.S. 61/582,023 filed Dec. 30, 2011 and U.S. 61/582,047 filed Dec. 30, 2011.

FIELD OF THE INVENTION

The present invention is directed to a liquid-absorbing article. More specifically, the present invention is directed to a liquid-absorbing article for use in personal care absorbent products such as diapers, training pants, sanitary napkins, incontinence garments, bandages and the like. The invention also relates to a process for making said article.

BACKGROUND OF THE INVENTION

A disposable diaper will conventionally comprise a backsheet which is impervious to liquids, typically a PE backsheet, a topsheet which is pervious to liquids and in contact with the body part, and sandwiched in between an absorbent core. The absorbent core is usually available in a core wrap, i.e. an envelope around the absorbing material. This core wrap or envelope typically comprises a bottom layer and a top layer, where the bottom layer contacts the backsheet and the top layer contacts the topsheet. An acquisition/distribution layer can also be present, where this layer can be in the core wrap (between the absorbent itself and the top layer) or outside the core wrap (between the top layer and the topsheet). It is also possible that the bottom layer be omitted and the backsheet then plays both roles of backsheet per se and bottom layer. It is also possible that the top layer be omitted and the topsheet then plays both roles of topsheet per se and top layer.

In disposable diapers, originally wood pulp fluff was used as the sole material for absorbing liquid, in this case urine. The problem with wood pulp fluff, however, was its poor wet strength and its tendency to collapse when wet which in turn often resulted in diaper leakage.

As the advances in diaper construction progressed, high absorbency materials such as fluid absorbent polymer particles or superabsorbents (Super Absorbent Polymers—SAP—) were mixed in with the wood pulp fluff to increase the overall liquid retention capacity of the diaper's absorbent core. This in turn allowed for a reduction in the overall thickness of the diaper by removing a portion of the wood pulp fluff and supplanting it with higher and higher quantities of the superabsorbent.

The development of SAP was such that an absorbent article especially an absorbent core without fluff (Fluff Free Core) is now possible, the SAP being the sole component for absorbing the liquid.

One problem when using superabsorbent is their need to swell or expand as they absorb liquid. If the particles are too closely confined, the particles cannot freely expand, and/or the swelled particles can cause rupturing of the materials around them which in turn can allow the superabsorbent to ooze out and possibly come in contact with the wearer. On the other hand, if the SAP particles are left free, then problems during transport and especially during liquid uptake will be generated. When simply placed between two sheets in a diaper, the SAP particles can flow and tend to accumulate at one place of the diaper, leaving the other place devoid of SAP, hence without liquid-absorbing capacity. Also, once the SAP particle has absorbed water and has swollen, these can create a barrier that blocks the passage of fluids into the centre of absorbent article especially the centre of the Fluff Free Core and therefore reduces or even block the absorption capacity for further acquisition of liquids ("gel blocking"). Additionally the swollen particles can flow and accumulate at one place of the diaper, with the same drawback as mentioned before. Another drawback is the unpleasant feeling generated by the accumulation of swollen material at one place of the diaper.

SAP distribution for use in a diaper is thus an issue in diaper manufacturing, and generally speaking in any absorbing article.

Livedo has developed a technology that is disclosed in EP1609448. It is disclosed a disposable absorbent article comprising an absorbent mat between a liquid-permeable top sheet and a liquid-impermeable back sheet, wherein: the absorbent mat includes (i) a sheet-shaped water-absorbent layer that contains SAP that is fluff-free and (ii) a fiber assembly layer that contains SAP and pulp fibers in this order from a top sheet side; and where the layer (i) includes a plurality of SAP presence regions in each of which the SAP powder is wrapped and a plurality of SAP absence regions between presence regions. The SAP is placed between non-woven fabric layers. Upon liquid uptake, the SAP increases the volume of the presence regions in the range of expansion allowed by the unwoven fabrics.

Another technology has been developed by Fameccanica that is disclosed in EP1974705. It is disclosed an absorbent element comprising: a first layer of sheet material presenting an array of hollowed formations with respective so-called "mouth parts"; SAP arranged in said hollowed formations; a second layer of sheet material, applied on said first layer of sheet material covering the mouth parts of said hollowed formations. The SAP expands in the hollowed formations and the second layer of sheet material being what is called "compliant" in an area corresponding to the mouth parts of said hollowed formations, enabling the further expansion of said masses of superabsorbent material beyond said hollowed formations. The term "compliant" is supposedly used to refer to a deformable part of the layer. The SAP is thus placed in a hollow cavity and will firstly expand to fill in the cavity and secondly by expanding the "compliant" part of the top layer.

According to the sole disclosed embodiment, the hollow formations are linked with adhesives, where one of the adhesive is a water-soluble glue. Upon contact with the liquid to be absorbed, the glue dissolves and the SAP can further expand to form one unique mass in a volume that can be defined as a tube.

The above techniques still do not completely solve the problem of the movement of the SAP in the cavities or in the absorbent article, before and/or after liquid absorption and the problem of gel blocking.

Consequently, there is a need for an improved liquid-absorbing article containing SAP where the SAP is maintained in place in an efficient manner.

A further object of the present invention is an absorbent article having improved properties in respect to the passage of fluids to the centre of the absorbent article or hollow cavities respectively and/or less or no gel blocking.

SUMMARY OF THE INVENTION

The invention thus provides an absorbent article (1) comprising:
- a first sheet layer (2) presenting an array of absorbent receiving pockets (4, 4a);
- masses (6) of superabsorbent material, which masses are placed in said absorbent receiving pockets (4, 4a);
- a second sheet layer (7) placed on top of the first layer;
- bonding beads (5) placed between the respective pockets; the first sheet layer (2) forming pleats (10) on the masses (6) of superabsorbent material.

According to one embodiment, the absorbent article (1) comprises:
- adhesive layers (3) and/or (8) between the first and second layers bonded in an area (9) in the vicinity of the beads (5); wherein the adhesive layers (3) and/or (8) delaminate in said area (9) upon exerting a pressure by the superabsorbent expansion.

According to one embodiment, the absorbent article (1) comprises two adhesive layers (3) and (8) applied respectively on sheet layers (2) and (7).

According to one embodiment, the absorbent article (1) comprises adhesive beads (5) in both the machine and transverse directions.

According to one embodiment, the bonding beads (5) define draining zones in the part of the sheet layers in correspondence.

According to one embodiment, the bonding beads (5) are adhesive beads.

According to one embodiment, the masses of superabsorbent material further comprise an adhesive.

According to one embodiment, the sheet layer (2) and/or (7) is/are non-woven.

According to one embodiment, the sheet layer (2) is impervious to liquids and the sheet layer (7) allows penetration of liquids into the masses of superabsorbent material.

According to one embodiment, the sheet layer (2) is a bottom layer and the sheet layer (7) is a top layer.

According to one embodiment, the adhesives (3, 8, 5) are non hydrosoluble.

According to one embodiment, the superabsorbent material comprises less than 30% fibers, preferably less than 10% fibers, more preferably is devoid of fibers mixed therewith.

According to one embodiment, the superabsorbent material has a centrifuge retention capacity of at least 24 g/g.

According to one embodiment, the superabsorbent material has an absorbency under load of at least 22 g/g, the absorbency being measured under a load of 49.2 $g/cm^2$ according to EDANA test method No. WSP 242.2-05 "Absorption under Pressure".

According to one embodiment, the superabsorbent material has a saline flow conductivity of at least $25 \times 10^{-7}$ $cm^3$ s/g.

According to one embodiment, the absorbent article (1) comprises an acquisition/distribution layer.

The invention also provides diaper, training pant, sanitary napkin, incontinence garment or bandage comprising the absorbent article of the invention.

The invention also provides a process for the manufacture of the absorbent article of the invention, comprising the steps of:
(1) providing a sheet layer (2)
(2) applying bonding beads (5) ensuring structural strength
(3) forming pockets (4, 4a) into said layer (2)
(4) filling the pockets with masses of superabsorbent material, the mass of superabsorbent material (6) representing, in volume, less than 70%, preferably less than 50% of the volume defined by the pockets before pleating step (7)
(5) providing a sheet layer (7)
(6) affixing the sheet layer (7) on the sheet layer (2) carrying the pockets (4, 4a)
(7) pleating the first sheet layer (2) on the masses (6) of superabsorbent material, the pleats being present in a zone that extends about the periphery of the pocket thus formed.

In the process of the invention pleats are formed by applying pressure in a direction that is substantially perpendicular to the plane of the layers so that the pleats (10) are built substantially parallel to the plane of the layers. Pleats (10) are generally formed from the parts of the sheets of the pockets that are perpendicular to the plane of the layers.

BRIEF DESCRIPTION OF DRAWINGS

FIG. 1B represents a schematic illustration of the top view of an absorbent article according to the invention.

FIG. 2A, FIG. 2B and FIG. 2C—represent the deformation of the article due to the swelling of the SAP.

FIG. 3—represents an overall view of the process of the invention for the manufacture of the article.

DESCRIPTION OF EMBODIMENTS OF THE INVENTION

The invention is now disclosed in more details below, in a non-limiting manner.

Reference is made to FIG. 1 which discloses the formation of the absorbent article of the invention according to one embodiment.

In an initial step, a first sheet layer (2) is provided. This first layer will serve as the bottom layer. It may be impervious to liquids, but this is not necessary in case of the presence of an impervious backsheet in the diaper for example.

This layer then receives a layer of adhesive (3). This adhesive is typically a hot-melt, as will be disclosed in more details below. The adhesive may be present on the entire surface or only at the vicinity of the sealed area. It is preferred that the adhesive be present on the entire surface (in a continuous or discontinuous manner). With this embodiment, the adhesive will receive the SAP and will adhere to it so that most of the SAP will be caused to adhere to the surface of the sheet layer. This will improve the SAP position and further prevent SAP from slipping within the disposable diaper.

The sheet layer (2) with the adhesive layer (3) is then formed into the desired shape. Different techniques may be used to form the shape of the pocket (4, 4a), as will be disclosed in more details below. In the embodiment that is disclosed, the step is disclosed in relation with the machine direction, forming bands, a specific step with respect to the transverse direction is applied later on.

Figure 1A:
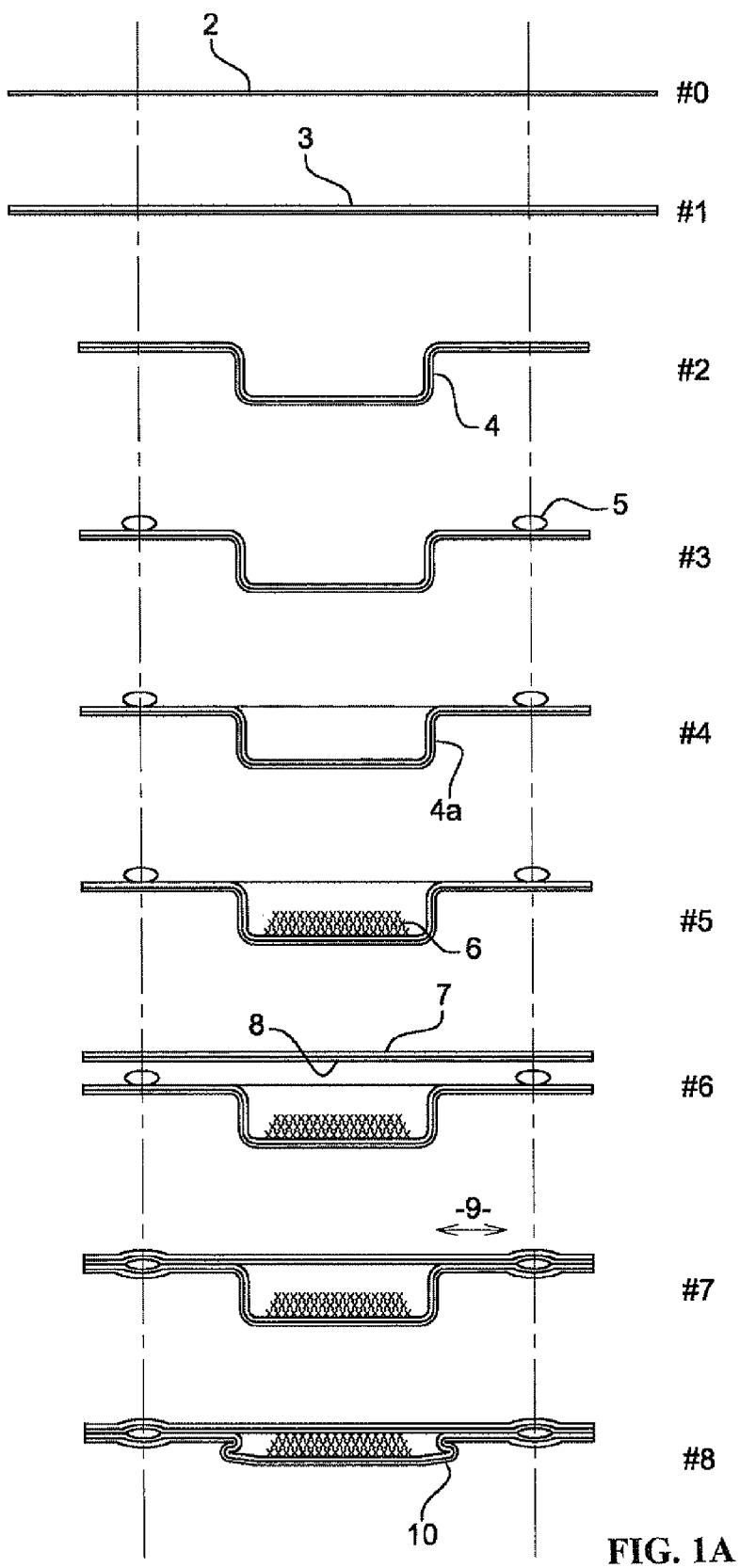
FIG. 1A represents the formation of the absorbent article of the invention.

Adhesive beads (5) (also known as adhesive ropes) are then applied at a location between the pockets (4, 4a) previously formed, as illustrated in FIG. 1a, which is a top view of an adsorbent core with pockets in rectangular shape and beads in the machine direction (MD) and transverse direction (TD). Standard techniques are used.

The beads ensure structural strength by keeping the sheet layers bonded during use. Furthermore the beads define draining zones, which improve the liquid distribution throughout the absorbent article and therefore improve passage of fluids to the centre of the absorbent article or hollow cavities respectively and reduce or avoid gel blocking.

The step of forming the pockets in the transverse direction is then performed; this step is optional but preferred. The step of adhesive beads deposition can be performed before or after the step of forming the transverse direction forms for the pockets. It may also be performed at about the same time.

The pockets thus formed can have various shapes and forms. For example, the pockets can be rectangular or square in shape with varying lengths of their respective sides. For example the length may vary from 10 mm×10 mm to 10 mm×80 mm, including 20 mm×20 mm to 20 mm×60 mm or 20 mm×20 mm to 40 mm×40 mm or 20 mm×40 mm with varying shapes, in any direction. The depth of the final pocket depends e. g. on the mass of SAP material to be filled in. For example for baby diapers a depth from 1 mm to 5 mm (once finally formed, i.e. pleated or calendered) may be preferred. Any other desired geometric forms and patterns are conceivable. The pockets may assume any desired shape in terms of area, for example circles, ellipses, rectangles, squares, triangles (viewed from above). Particular preference is given to any desired polygons or mixtures of polygons. Particular preference is also given to the application of one or more continuous strips in machine running direction, the strips running parallel to one another. Furthermore it is preferred that the adhesive beads are forming a connected network surrounding the pockets. After SAP is applied the pockets may be formed as cushions for example those which are arranged like cushions comprising SAP in the cushions. The cushions or the heaps of SAP applied assume any desired shape in terms of area as mentioned above.

Thus a Livedo type pocket is possible; in this case the pocket will be elongated, e.g. from 10-80 mm×100-400 mm.

The SAP is then placed in the thus-formed pockets, using an appropriate dosing device, as will be disclosed in more details below.

The second sheet layer (7) receives first an adhesive layer (8). The second sheet layer is typically water-permeable so as to allow the fluids to penetrate through and reach the SAP. This second sheet will typically serve as the top layer. The adhesive layer will not be complete or will be porous, so as to allow transfer of fluid through the sheet layer. The adhesive layer (8) is optional and may be omitted.

The second sheet layer (7) with the adhesive layer (8) is then affixed onto the first sheet layer (2) with the pockets (4, 4a) containing the SAP (6) and bearing the beads (5). This is done in an area (9) in the vicinity of the beads (5)

Calendering is then performed on the sandwich thus formed, ensuring the bonding of the two sheet layers.

Pleating (or compacting) is finally performed, so as to create pleats (10) and tightly contain the SAP in the pockets for example for further fixation of the SAP in the pockets. This pleating step may be omitted if no pleat is required.

Figure 12:
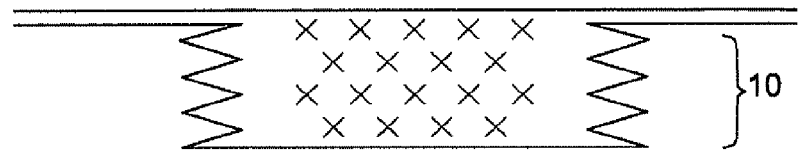
FIG. 12—is a schematic cross-sectional view of the pockets with the pleats.

Pleats (10) are usually formed when the mass of SAP after calendering, but before pleating, is not in contact over substantially all its upper surface with the top layer and/or the SAP mass represents, in volume, less than 70%, preferably less than 50% of the volume defined by the pockets before pleating, typically between 5 and 45%, e.g. between 10 and 40%. Pleats (10) will be considered to be formed and existing when the mass is in contact over substantially all its upper surface with the top layer and/or the free volume in the pleated pocket is substantially zero. Pleats are formed by applying pressure in a direction that is substantially perpendicular to the plane of the layers so that the pleats (10) are built substantially parallel to the plane of the layers. Pleats (10) are thus formed from the parts of the sheets of the pockets that are perpendicular to the plane of the layers. Pleats are present in a zone that extends about the periphery of the pocket thus formed. There can be 1, 2, 3, 4 and even up to 10 or more pleats, e.g. up to 20 pleats. Typically the number of pleats is from 5 to 10. Pleats are also depicted in FIG. 12, which is a cross-sectional view in perspective of the pockets with the pleats. In FIG. 12 the walls (the parts of the sheets of the pockets that are perpendicular to the plane of the layers before calendering) are represented with the pleats.

In the above embodiment, both pleats and adhesive distribution allows the SAP expansion. It is possible to have only the pleats (10), or only the adhesive distribution. Having only the pleats is achieved by omitting the adhesive layer (8) and keeping only the beads. Having only the adhesive distribution is achieved by selecting the proper amount of SAP given the size and shape of the pocket, so as to fill in the required amount such that the two sheets are held together without the pleats. It is preferred to have both.

Reference is made to FIG. 2 which discloses the swelling of the SAP during liquid absorption, the enlarged view at the bead level being represented. The first step, identified as 2a, is the deploying of the pleats (if any). The second step, identified as 2b, is the progressive peel-off in the area (9) close to the beads. The first and second steps can be simultaneous, sequential or off-set, depending on the strength of the adhesive, the swelling rate, the pleats number, etc. The peel-off takes places typically at the interface between the two adhesives layers (3) and/or (8) when both are used, or at the interface between the adhesive(s) layer(s) (3) and/or (8) and the adjacent sheet layer; or in one of the adhesive(s) layer(s) (3) and/or (8) (from adhesive to cohesive failure in the adhesive layer). At step (2c), the peel-off and/or deploying is complete, the two sheets being remaining bonded only at the bead level.

The strong bonding due to the beads will maintain the integrity of the article. Furthermore the draining zones will also be maintained. Further expansion is still possible using the elasticity of the sheet layers, if available. The progressive peeling-off is obtained by adjusting the surface weight of the adhesive layers (3) and/or (8), it being known that the peeling force is usually proportional to the surface weight. The peeling-off force is also adjusted by the adhesive coating method, the type of adhesive, as is known for the skilled man. The type of support, especially non-woven, is also to be taken into account to have an adhesive failure mode rather than a cohesive failure mode during peel-off. The peel force is typically from 2 to 5N/25 mm, as measured using a tensometer (T-peel at 300 mm/mn) at 23° C./50% RH.

For example, a pressure sensitive adhesive (Bostik adhesive H4245, a SBS-based adhesive with hydrogenated hydrocarbon resins and naphthenic oil) is applied directly on the bottom layer of the assembly (a spunbond PP nonwoven of 14.5 g/m$^2$ from DOUNOR—France) as a full slot coating of about 5 g/m$^2$. The same adhesive is also applied directly on the top layer of the assembly (a spunmelt PP hydrophilic nonwoven of 10 g/m$^2$ with a strike-through time of about 3 s—according to EDANA recommended test method ERT 150.5—from DOUNOR—France) as a combed slot coating (2 mm on/2 mm off) of about 5 g/m$^2$. The top layer was mounted on the bottom layer and pressed using a pressure roll (weight: 2 kg, width 6 cm), 2 passes. After dwelling 24 hours at 23° C./50% RH, the assembly was cut to 25 mm in width and peeled on a tensometer (T-peel at 300 mm/mn) at 23° C./50% RH. Typical peel value is 3.3 N/25 mm with cohesive failure in the adhesive layer. In another embodiment, the previous assembly was reiterated but inserting between the adhesive-coated top and bottom layers, a bead of adhesive (Bostik adhesive H4245 is used) of about 0.4 g/linear meter, 2 mm in width. The same method is used to create the assembly (pressure roll, 2 passes), making sure that the adhesive bead is placed in the middle of the pressed laminate. Same peel method is used, making sure that the adhesive bead is placed in the middle of the tested laminate. Typical peel value is 4.6 N/25 mm, with failure of the non-woven in this case, at the bead level. Hence, peel off of the two layers is first carried out, with a cohesive failure (in the adhesive layers), and then the beads will play their role of strong bond between the two layers (cohesive failure). The peeling off value is typically from 1 to 10 N/25 mm. The bead will typically provide for a force that is 1 to 5 N/25 mm higher than the peeling off value above.

The progressive expansion, which can be obtained by the pleats, the adhesive layers, or both, is valuable. Indeed, compared to existing solutions, the SAP is maintained in the pockets, unlike the Fameccanica embodiment disclosed above. The expansion of the SAP is also made easier, compared to the Livedo solution disclosed above, since the size of the pocket can be adapted thanks to the pleats and/or the adhesive layers. SAP is maintained in a very efficient way in the pockets formed in the invention, being prevented from slipping and/or aggregating at one place in the article. Furthermore especially due to the beads the liquid distribution e. g. throughout the absorbent article is improved and therefore the passage of fluids to the centre of the absorbent article or the pockets respectively improved and gel blocking reduced or avoided.

The steps for manufacturing the article of the invention and the various elements thereof are disclosed in more details below.

The SAP that is used in the invention is any product that is able to absorb water to a significant amount. A typical SAP will absorb water from 10 to 50 times its dry volume, typically from 20 to 40 times (the ratio can be higher if expressed in terms of weight ratios). For example, 15 g of SAP may retain 400 cc of fluid (tested as 4 successive wettings, 4×100 cc). BASF is exemplary of a company supplying SAP. SAP is generally available as a powder, with varying particle size (e.g. more than 60% of the particles flow through a mesh from 100 μm to 850 μm). Typically SAPs are (meth)acrylic polymer, especially alkali metal salts of polyacrylic acids. Core-shell polymers can be used, where the inner is absorbing and the outer is an osmotic membrane. SAPs are well known for the skilled man.

The production of fluid-absorbing polymer particles (Super Absorbent Polymers—SAP—) is likewise described in the monograph "Modern Superabsorbent Polymer Technology", F. L. Buchholz and A. T. Graham, Wiley-VCH, 1998, pages 71 to 103.

The fluid-absorbing polymer particles are produced, for example, by polymerizing a monomer solution or suspension comprising a) at least one ethylenically unsaturated monomer which bears acid groups and may be at least partly neutralized, b) at least one crosslinker, c) at least one initiator, d) optionally one or more ethylenically unsaturated monomers copolymerizable with the monomers mentioned under a) and e) optionally one or more water-soluble polymers, and are typically water-insoluble.

The fluid-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a).

Useful purification methods are disclosed in WO 2002/055469 A1, WO 2003/078378 A1 and WO 2004/035514 A1.

A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tatrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)ethylenediaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for cross-linking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

The initiators are used in customary amounts, for example in amounts of from 0.001 to 5% by weight, preferably from 0.01 to 2% by weight, based on the monomers a).

Particularly preferred initiators c) are azo initiators such as 2,2'-azobis[2-(2-imidazolin-2-yl)propane]dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Bruggolite® FF6 and Bruggolite® FF7 (Bruggemann Chemicals; Heilbronn; Germany).

Ethylenically unsaturated monomers d) copolymerizable with the ethylenically unsaturated monomers a) are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

Useful water-soluble polymers e) include polyvinyl alcohol, polyvinylpyrrolidone, starch, starch derivatives, modified cellulose, such as methylcellulose or hydroxyethylcellulose, gelatin, polyglycols or polyacrylic acids, polyesters and polyamides, polylactic acid, polyvinylamine, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 85 mol %, for "acidic" polymer gels more preferably from 30 to 60 mol %, most preferably from 35 to 55 mol %, and for "neutral" polymer gels more preferably from 65 to 80 mol %, most preferably from 70 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts, such as the salt of triethanolamine. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA recommended test method No. WSP 230.3-10 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (fines) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of EDANA recommended test method No. WSP 220.3-10 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small particle size lower the saline flow conductivity (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment, polyvalent cations are applied to the particle surface in addition to the surface postcrosslinkers before, during or after the surface postcrosslinking.

The polyvalent cations usable are, for example, divalent cations such as the cations of zinc, magnesium, calcium and strontium, trivalent cations such as the cations of aluminum, tetravalent cations such as the cations of titanium and zirconium. Possible counterions are, for example, chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations. A single metal salt can be used as well as any mixture of the metal salts and/or the polyamines above.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal drying is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Nara paddle driers and, in the case of using polyfunctional epoxides, Holo-Flite® dryers are preferred. Moreover, it is also possible to use fluidized bed dryers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed dryer.

Preferred drying temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

It is preferable to cool the polymer particles after thermal drying. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures of in the range from 20 to 150° C., preferably from 40 to 120° C., more preferably from 60 to 100° C., most preferably from 70 to 90° C. Cooling using warm water is preferred, especially when contact coolers are used.

Subsequently, the surface postcrosslinked polymer particles can be classified again, excessively small and/or excessively large polymer particles being removed and recycled into the process.

To further improve the properties, the surface postcrosslinked polymer particles can be coated and/or remoisturized.

The optional remoisturizing is carried out preferably at 30 to 80 polymer particles can be coated by small and/or excessively large polymer particles being removed and recycled into the process suitable coolers are, for example, Hosokawa Bepex® horizontal padwater already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for controlling the acquisition behavior and improving the permeability (SFC or GBP) are, for example, inorganic inert substances, such as water-insoluble metal salts, organic polymers, cationic polymers and polyvalent metal cations. Suitable coatings for improving the color stability are, for example reducing agents and antioxidants. Suitable coatings for dust binding are, for example, polyols. Suitable coatings against the undesired caking tendency of the polymer particles are, for example, fumed silica, such as Aerosil® 200, and surfactants, such as Span® 20. Preferred coatings are aluminium monoacetate, aluminium sulfate, aluminium lactate, Brüggolite® FF7 and Span® 20.

Suitable inorganic inert substances are silicates such as montmorillonite, kaolinite and talc, zeolites, activated carbons, polysilicic acids, magnesium carbonate, calcium carbonate, calcium phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the fluid-absorbent polymer particles are coated with inorganic inert substances, the amount of inorganic inert substances used, based on the fluid-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoro-ethylene. Other examples are styrene-isoprene-styrene block-copolymers or styrene-butadiene-styrene block-copolymers.

Suitable cationic polymers are polyalkylenepolyamines, cationic derivatives of polyacrylamides, polyethyleneimines and polyquaternary amines.

Polyquaternary amines are, for example, condensation products of hexamethylenedi-amine, dimethylamine and epichlorohydrin, condensation products of dimethylamine and epichlorohydrin, copolymers of hydroxyethylcellulose and diallyldimethylammo-nium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, poly-functional acids or poly-functional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the fluid-absorbent polymer particles are coated with a cationic polymer, the use amount of cationic polymer based on the fluid-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable polyvalent metal cations are $M^{2+}$, $Ca^{2+}$, $Al^{3+}$, $Sc_{3+}$, $Ti_{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, nitrate and sulfate. The metal salts are preferably used as a solution or as a stable aqueous colloidal dispersion. The solvents used for the metal salts may be water, alcohols, dimethylfor-mamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the fluid-absorbent polymer particles are coated with a polyvalent metal cation, the amount of polyvalent metal cation used, based on the fluid-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophos-phite, salts of sulfinic acids, for example the disodium salt of 2-hydroxy-2-sulfinato-acetic acid, and addition products of aldehydes, for example the disodium salt of 2-hy-droxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Bruggemann Chemicals; Heilbronn; Germany).

The reducing agents are typically used in the form of a solution in a suitable solvent, preferably water. The reducing agent may be used as a pure substance or any mixture of the above reducing agents may be used.

When the fluid-absorbent polymer particles are coated with a reducing agent, the amount of reducing agent used, based on the fluid-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the fluid-absorbent polymer particles only insignificantly. The polyols are preferably used as a solution in aqueous or water-miscible solvents.

When the fluid-absorbent polymer particles are coated with a polyol, the use amount of polyol, based on the fluid-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Moreover, it is also possible to use a fluidized bed for mixing.

The water-absorbing polymer particles have a moisture content of preferably 0 to 15% by weight, more preferably 0.2 to 10% by weight, most preferably 0.5 to 8% by weight, the moisture content being determined by EDANA (European Disposables and Nonwovens Association) recommended test method No. WSP 230.2-05 "Moisture Content"

The fluid-absorbing polymer particles have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the fluid-absorbing polymer particles is typically less than 60 g/g. The centrifuge retention capacity (CRC) is determined by EDANA recommended test method No. WSP 241.2-05 "Centrifuge Retention Capacity".

The fluid-absorbing polymer particles have an absorbency under a load of 49.2 g/cm$^2$ of at least at least 18 g/g, typically at least 20 g/g, preferably at least 22 g/g, more preferably at least 24 g/g, most preferably at least 25 g/g. The absorbency under a load of 49.2 g/cm$^2$ of the fluid-absorbing polymer particles is typically less than 35 g/g. The absorbency under a load of 49.2 g/cm$^2$ is determined analogously to EDANA recommended test method No. WSP 242.2-05 "Absorption under Pressure".

The fluid-absorbent polymer particles have a saline flow conductivity (SFC) of typically at least $20 \times 10^{-7}$ cm$^3$ s/g, preferably at least $25 \times 10^{-7}$ cm$^3$ s/g, preferentially preferably at least $30 \times 10^{-7}$ cm$^3$ s/g, most preferably at least $50 \times 10^{-7}$ cm$^3$ s/g. The saline flow conductivity (SFC) of the fluid-absorbent polymer particles is typically less than $500 \times 10^{-7}$ cm$^3$ s/g. The saline flow conductivity is basically determined according to EP 0 640 330 A1, as the gel layer permeability of a swollen gel layer of fluid-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically. The saline flow conductivity (SFC) is calculated as follows:

$$SFC\ [cm^3 s/g] = (Fg(t=0) \times L0)/(d \times A \times WP)$$

where Fg(t=0) is the flow rate of NaCl solution in g/s, which is obtained by means of a linear regression analysis of the Fg(t) data of the flow determinations by extrapolation to t=0, LO is the thickness of the gel layer in cm, d is the density of the NaCl solution in g/cm$^3$, A is the surface area of the gel layer in cm$^2$ and WP is the hydrostatic pressure over the gel layer in dyn/cm$^2$.

The fluid-absorbent polymer particles have a gel bed permeability (GBP) of 10 to 1000 darcies. Whereas fluid-absorbent polymer particles with a gel bed permeability (GBP) of 10 to 100 are preferred. The gel bed permeability (GBP) is determined according to US 2005/0256757.

The SAP may also be the one disclosed in WO2010/133529, from page 6 line 1 to page 15 line 16, incorporated herein, by reference.

The SAP load may vary within broad limits. For example, for a baby diaper, the amount of SAP usually used is from 8 to 20 g, preferably from 11 to 18 g, more preferably from 12 to 15 g.

The invention also uses sheet layers, one typically as a bottom layer and one typically as a top layer. Typically, both sheets are non-woven. Non-woven can be manufactured using different technologies and one can cite staple non-woven, spunbonded non-woven, spunlaid non-woven, air-laid non-woven, and the like. Bonding can be mechanical (e.g. entanglement), thermal, ultrasonic, chemical, and the like. Non-woven are well-known for the man skilled in the art. The non-woven used can be standard or can be structured, and can also be already embossed if needed.

The non-woven can be pervious to liquids or impervious to liquids. The skilled man will select the fibers to be used to match the requirements. Hydrophilization of fibers is known to render fibers suitable for the manufacture of liquid-pervious non-woven.

Fibers can be customary synthetic or semi-synthetic fibers, such as polyesters, polyolefins and rayon, or customary natural fibers, such as cotton. In the case of nonwoven materials, the fibers can be bonded by binders such as polyacrylates. Preferred materials are polyester, rayon, polyethylene and polypropylene. Examples of liquid-pervious layers are described, for example, in WO 99/57355 A1 and EP 1 023 883 A2.

Examples of liquid-impervious layer are layers consisting typically of hydrophobic polyethylene or polypropylene; other material can be used such as polyester and polyamide.

Multilayer structures are also possible, so as to provide for a specific aspect or feel on one side of the sheet and specific properties on the other side, e.g. with respect to adhesion.

The above Livedo reference EP1609448, as well as US2008/0045917 provide for disclosure of such non-wovens.

The top layer will be permeable to liquids, so as to allow the liquid being entrapped by the SAP. A possible non-woven for the top layer will be one with polyethylene or polypropylene fibers having received a hydrophilization treatment, or rayon or any other suitable fibers. The Livedo reference above contains a disclosure of possible top layers. The surface weight can vary between wide ranges, such as from 5 to 100 g/m², preferably from 10 to 50 g/m².

The bottom sheet layer will be impervious to liquids, as is usually the case, but not necessarily. A possible layer is a non-woven layer. A possible non-woven for the bottom layer will be one with polypropylene or polyester fibers, as is well-known for the skilled man. The Livedo reference above contains a disclosure of possible bottom sheet layers. The surface weight can vary between wide ranges, such as from 5 to 100 g/m², preferably from 10 to 50 g/m². The bottom sheet layer will also have a porosity to air that will be controlled. This will assist in forming the pockets and filling in the SAP, as will become more apparent below.

The adhesives used in the invention are known for the skilled man. The first type of adhesive is used for the beads. The adhesive for the beads is typically a hot-melt. It may be typically a PSA (Pressure Sensitive Adhesive). The preferred adhesive is thus a HMPSA. Exemplary HMPSA that may be used for the beads is an SBS-based adhesive with hydrogenated hydrocarbon resins and naphthenic oil. The process for adhesive deposition is known to the skilled man, and the lines can be continuous or broken, preferably continuous. The linear weight is from 0.1 to 5 g/linear meter.

Beads can be present in the machine direction (MD), transverse direction (TD) or both. The beads ensure geometrical stability of the absorbent article. The beads also ensure a draining function. The liquid can migrate within the thickness of the sheet layer esp. the non-woven. At the beads level, the liquid will be guided along the pathways defined by the beads, and draining pathways will then be defined. This ensures a more uniform distribution of the fluid over the entire absorbent article.

Similar adhesives are used for adhesives layers (3) and (8) (if present), which are of a nature that allows progressive peeling-off. The adhesives may not be the same for the top layer and the bottom layer. The adhesive may be deposited using techniques known to the skilled man. The coating can be total or partial (multi lines, multi dots, according to specific patterns, MD, TD, spiral spray, porous coating, foam coating, and the like). The adhesive, if used on the top layer, will be such that fluids will be able to go through the top layer. Hence, the coating for the top layer is usually an open coating. The surface weight will usually control the forces for peeling off, and typical values are from 5 to 60 g/m2, preferably from 10 to 20 g/m2. Adhesives used with the sheet layers (beads or deposited on the sheet layer) are preferably not hydrosoluble.

Hot melts are preferred, especially Pressure Sensitive Adhesives (PSA, especially HMPSA).

Very generally speaking, and without this being limiting, the hot melt adhesives comprise:

(a). Polymers such as EVA, PE, PP, EEA (ethylene ethyl acrylate) and the thermoplastic elastomers or rubbers which are (block) styrene copolymers such as SIS, SIBS, SEPS, SBS, SEBS, or butadiene-based polymers or, yet again, ethylene-propylene copolymers such as EPR, and Olefin Block Copolymer OBC. A chemical modification such as maleic anhydride modification is possible.

A typical average molar mass in weight MW is between 60 kDa and 400 kDa.

They can make up from 10 to 80%, preferably 15 to 40% of the formulation and their purpose is to provide: mechanical strength, flexibility, barrier properties, brilliance and viscosity control.

(b). tackifying resins which can be polar or non-polar resins. Polar resins can be (i) rosins of natural or modified origin, such as for example the rosin extracted from the gum of pinewood, their polymerized, dimerized, dehydrogenated, hydrogenated derivatives or esterified by monoalcools or polyols like glycol, glycerol, pentaerythritol; (ii) terpenic resins generally resulting from the hydrocarbon polymerization terpenic in the presence of catalysts of Friedel-Crafts like the mono-terpene (or pinene), the alpha-methyl styrene, and possibly modified by phenol action. Non-polar resins can be (iii) resins obtained by hydrogenation, polymerization or copolymerization (with an aromatic hydrocarbon) of mixtures of unsaturated aliphatic hydrocarbons resulting from oil cuts; (iv) terpenic resins generally resulting from the terpenic hydrocarbon polymerization in the presence of catalysts of Friedel-Crafts such as for example mono-terpene (or pinene), copolymers containing natural terpenes, for example styrene/terpene, the alpha-methyl styrene/terpene and the vinyl toluene/terpene.

Tackifying resins can be natural (rosin esters, terpene or terpene-phenolic esters), or oil-based, aliphatic or aromatic. They make typically up from 10 to 80%, preferably 30 to 60%, of the formulation. They increase the hot tack, adherence and control cohesion.

(c). Paraffins and waxes, which can make up from 0 to 20% of the formulation. They play a role in providing barrier, rigidity and hot melt hardness properties.

(d). Plasticizers such as oils which can make up some 0 to 30% of the formulation. They control hot melt flexibility and viscosity.

(e). Anti-oxidants which may make up from 0.2 to 2% of the formulation. They stabilize the components when hot and when cold.

(f). Fillers which may make up part of the formulation when particular properties are desired such as UV-resistance (oxidation resistance), flame proofing, anti-allergy properties, rheology modification, etc.

An hot-melt may have the following composition: 15 to 40% thermoplastic polymer, 30 to 60% tackifying resin, 30% or lower of other constituents: plasticizing oil, anti-oxidation agents, additives etc.

Residual tack can be controlled by adjusting the ingredients and the formulation.

An adhesive may also be used with the SAP. This may assist in reducing the SAP movements. This can be, as disclosed above an HMA, HMPSA. It may also be water based (WB), and for example it can be a WBPSA. The adhesive used together with the SAP can be hydrosoluble. This adhesive can be deposited at the same time the SAP is placed in the formed pockets. This embodiment will allow a tighter holding of the particles or grains of SAP, which is beneficial for the process and/or design.

With reference to FIG. 3, an overall view of the process is provided. In FIG. 3 are represented the rolls C1, C2, C3, C4, C5 and C6, and associated slender rolls for rolls C1, C3 and C6. Nip points A, B, C D and E, corresponding respectively to the nip between rolls C1 and slender roll, C3 and C4, C3 and slender roll, C3 and C5, and C6 and slender roll are also shown in FIG. 3. Are also represented sheets (2) and (7) when supplied from appropriate sources. Each sub-step of FIG. 1 can also be found in a corresponding manner in FIG. 3. Each step will then be disclosed in a more detailed manner below. One will understand that the optional steps in FIG. 1 are similarly optional in FIG. 3.

Figure 4:
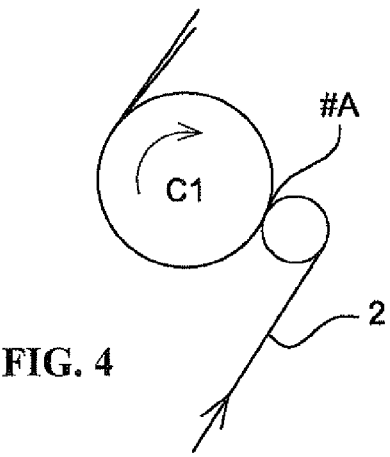
FIG. 4—represents the bottom layer supply step.

With reference to FIG. 4, the initial bottom layer supply step is disclosed. Sheet layer (2) is unrolled under mild tension up to a nip point #A between roll C1 and associated slender roll. Roll C1 is preferably smooth and comprises for example a rubber sheath.

Figure 5:
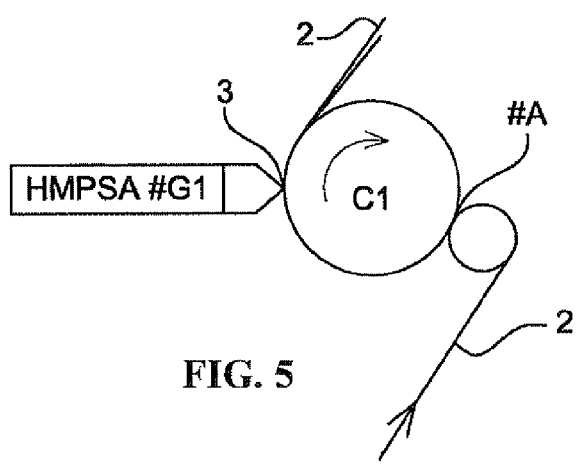
FIG. 5—represents the adhesive layer (3) distribution step.

With reference to FIG. 5, the sheet layer (2) (bottom layer) will receive an adhesive layer (3). This adhesive can be HMPSA and is represented by the deposition of glue G1. This takes place while the bottom layer is on roll C1, after nip point A. This adhesive will serve the purpose of retaining as much as possible the SAP that will be distributed in the pockets at point #B (see below). The adhesive coating is performed using standard techniques, as indicated above. The surface weight of the adhesive layer (3) will serve the purpose of tailoring the peeling force between the two sheets during the swelling of the SAP. In one embodiment, the adhesive is deposited as a foamed product. A foamed product will offer, for a given thickness, savings in adhesive amount, a higher tackiness, a lower cohesion (entrapping of SAP), and a lower flow (SAP particles coating should be avoided since their specific surface is one driving factor for the liquid absorption).

Figure 6:
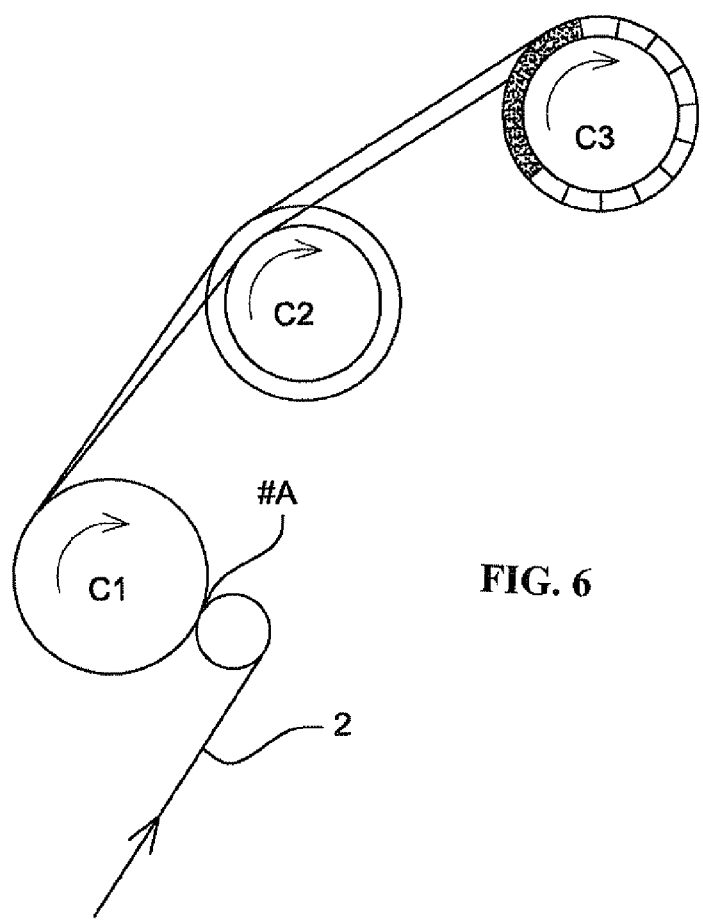
FIG. 6—represents the forming of the sheet layer (2) onto roll C2.

With reference to FIG. 6, the sheet layer (2) (bottom layer) is formed onto a roll C2 so as to impart the lengthwise profile of the pockets. Roll C1 has a rotating speed which is higher than the rotating speed of roll C3. The difference in rotating speed allows material to be present for forming the vertical walls of the pockets. Roll C2 will have a rotating speed slightly above the speed of roll C1 so as to generate a tension necessary for the forming. The friction being higher in the upper part of roll C2 will also ensure tensioning the bottom layer during deposition of the adhesive beads (below). Roll C2 can receive a non skid coating.

Figure 7:
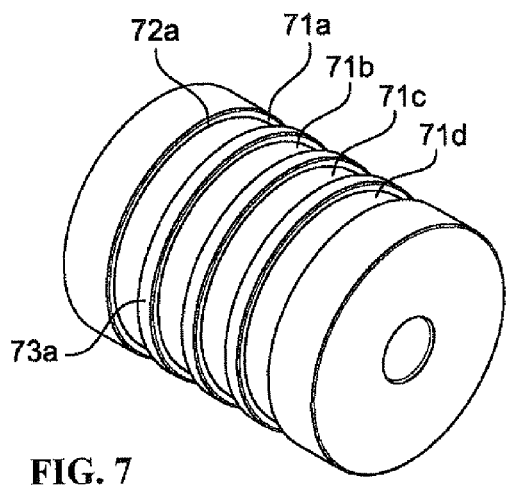
FIG. 7—represents an enlarged view of roll C2.

In FIG. 7, the roll C2 has grooves 71a, 71 b, 71c, 71d. Each groove has a valley, represented here with a square shape, but tapered valleys are possible, and the angles can be smoothed if desired. Is represented valley 72a corresponding to groove 71a. A corresponding peak 72a is represented, between two adjacent valleys. The web that is obtained after roll C2 hence exhibits ribs or corrugations. The web will match the groove due to the difference in friction between the top and the bottom of the grooves and the difference in winding speeds. The difference in winding speeds between the rolls C2 and C3 allows material to match the inner of the grooves. The width of the web is reduced due to the formation of ribs/corrugations in the grooves; the difference in rotating speeds provides for a relaxation of the web tension and allows for such formation. The sheet layer (2) (with the adhesives (3) and/or (5)) is unstressed between rolls C2 and C3, where roll C3 has a rotating speed below the one of roll C2, as previously indicated. The difference in rotating speeds between rolls C2 and C3 is dictated by the amount (or length) of sheet layer that is necessary to form the other part of the vertical walls of the pockets. The two nip points #A and #D (calendering, see below, nip point #D is not represented on FIG. 6) will act as fixed points to impart the geometry to the sheet between the two nip points.

Figure 8:
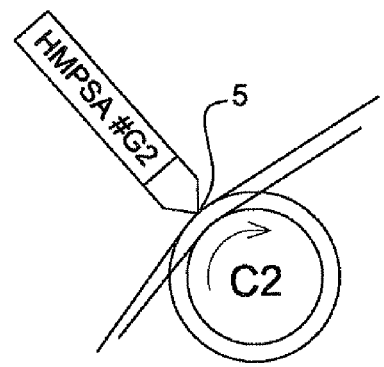
FIG. 8—represents the beads deposition step.

Roll C2 can be obtained by stacking discs of varying thicknesses and diameters (corresponding to width and depth of the pockets). This allows changing rapidly the geometry of the article without the need to revert to a complete change of set of rolls. With reference to FIG. 8, the beads deposition is disclosed. Lengthwise beads are deposited using standard techniques. Because roll C2 has an adapted speed, the tension on the outer surface is suited for receiving the adhesive beads. The beads may not need to be necessarily linear, or continuous. They can be in the form of zigzags, and can be as dots. Beads deposition takes place on the sheet at locations corresponding to, or close to, the peaks 72a.

An alternative embodiment is one where the adhesive beads are replaced by another bonding process. As bonding process, one can use the heat-sealing, the ultrasound sealing, sewing, carding the two non-woven together. Bonding without adhesives is carried out generally after the calendering step.

With reference to FIG. 6 (see above), the pockets formation is disclosed, where the pockets are formed mainly by roll C3. In a manner similar to the forming according to MD (Machine Direction), the forming of the pockets in the TD (Transverse Direction) is carried out using a roll C3 formed from stacking discs with selected geometry, forming a matrix.

Figure 9A:
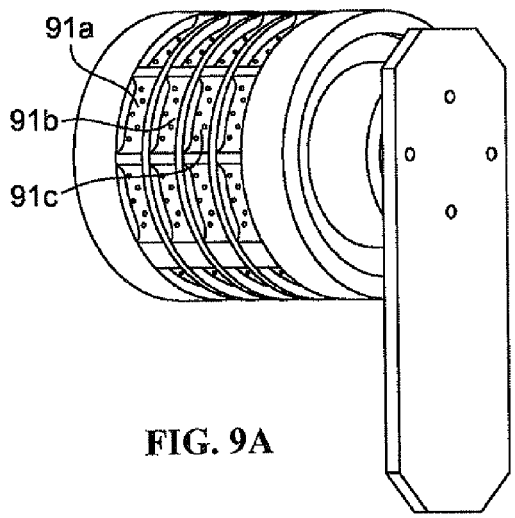
FIG. 9A and FIG. 9B—represent the roll C3 for two different embodiments of the invention.

With reference to FIG. 9a, a roll C3 is disclosed which is a matrix. The bottom part of the recesses (91a, 91b, 91c) in the roll C3 is equipped with holes, allowing applying a vacuum. Applying a vacuum will serve attracting the sheet layer so as to conform it to the shape of the matrix, to define the pockets. The air porosity (Gurley porosity) of the bottom layer non-woven will be adapted such that the vacuum applied in the central part of the roll C3 is sufficient to press the sheet against the roll by suction. The applied vacuum will also serve when the SAP is distributed into the pockets thus formed (see below). The applied vacuum can be obtained with an inner drum or mandrel inserted into the roll, which can be segmented so as to apply vacuum only to those part of the roll in need thereof. The segment with the vacuum can thus represent between 30° and 180°, preferably between 60° and 120°.

A vacuum segment can be of the type disclosed in the prior art documents mentioned above, see EP-A-1621166 and EP-A-1621167. Roll C3 can be varied in dependence on the desired shape or geometry of the pockets.

Figure 9B:
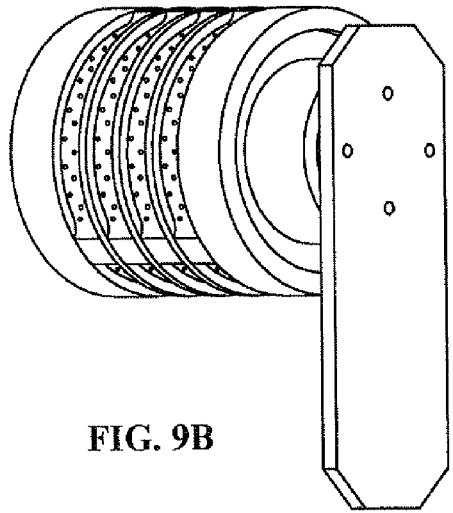

FIG. 9b represents a roll C3 with elongated shapes, rather than matrix shapes.

Figure 9C:
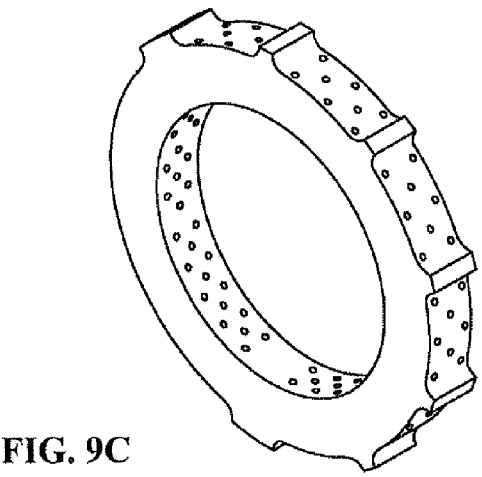
FIG. 9C and FIG. 9D—represent the respective discs, corresponding to FIG. 9A and FIG. 9B.
Figure 9D:
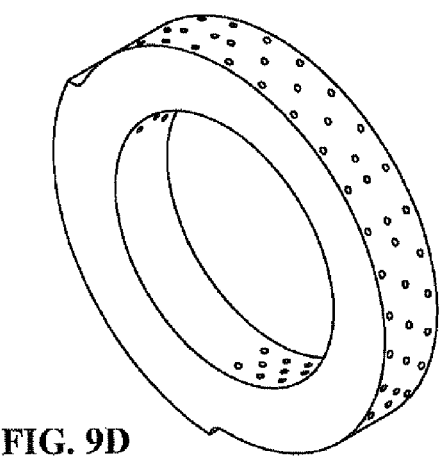

The roll C3 can be obtained in a manner similar to roll C2, i.e. by using discs that are stacked on an axis. FIGS. 9c and 9d represent the respective discs, corresponding to FIGS. 9a and 9b.

Figure 10:
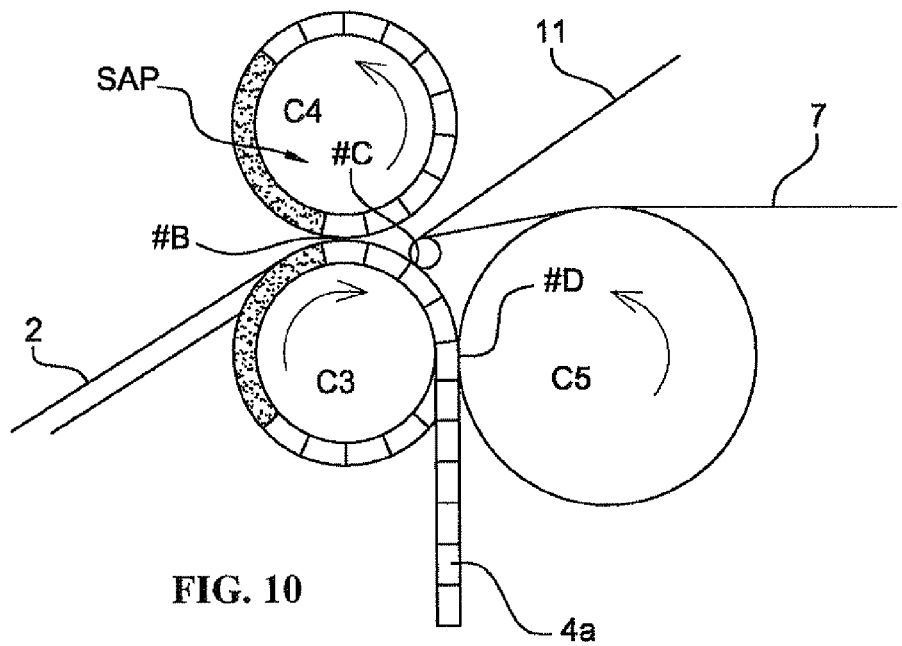
FIG. 10—represents the SAP distribution step and the calendering step, as well as the optional ADL deposition step.

With reference to FIG. 10, is disclosed the distribution of the SAP. SAP is distributed from roll C4, which is counter-rotating with respect to roll C3. Rotating speeds of rolls C3 and C4 are adapted one to the other. The two rolls are usually not in contact, a small gap existing between the two, so as to adapt for varying thicknesses for the bottom layer (2). One possible technique for dispensing SAP is the one disclosed in document U.S. Pat. No. 7,744,713, incorporated herein by reference. Vacuum being applied in the forming roll, this will also assist the SAP to be kept in place (with the Gurley porosity of the bottom layer being adapted to let the vacuum have an effect on holding in place the SAP).

It is also possible that the forming of the pockets be done by other processes, such as the embossing process (albeit this is not preferred). For example; the pocket forming roll or system can be the one disclosed in the cited patent U.S. Pat. No. 7,744,713.

With reference to FIG. 10 is also disclosed the bringing into contact of the top layer (sheet layer (7)). The top layer is displayed facing the bottom layer at a nip point #C, before calendering. Point #C is preferably as close as possible to nip point #B, so as to avoid polluting adhesive parts (if any) with the powdery SAP. The top layer (7) is brought under tension on the top of the pockets formed before and is tensioned by passing over a slender roll (which may have a banana shape). Tension is preferably applied to as to minimize the effect of the vacuum on the top layer to be applied (tension will avoid waves that could otherwise form due to the vacuum). The slender roll may also comprise rigs, so as to form a top layer with pleats within the thickness (to provide for further expansion).

With reference to FIG. 10, is also disclosed the calendering step. A pressure is applied between rolls C3 and C5 to proceed with the fixing of the top layer onto the bottom layer, whereby closed pockets (4a) are formed.

Is also represented as a further, optional, embodiment, the providing of the acquisition distribution layer ADL (11). This layer is supplied at nip point #C so as to be formed into a sandwich at that point. This ADL will preferably receive adhesives on both faces, but can also be fixed using any of the bonding system discussed above.

Figure 11:
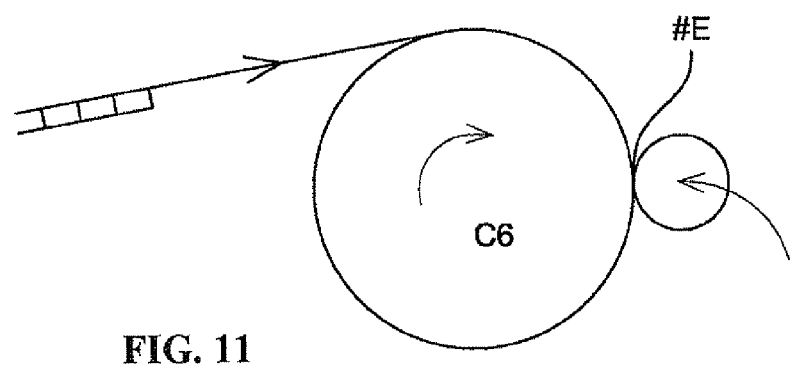
FIG. 11—represents the finishing step.

With reference to FIG. 11, is disclosed the finishing step. The compacting (pleats formation) is carried out during winding under tension of the finished product. A pressing roll C6 is used to impart pressure at point #E during winding.

Two optional steps can be present (not shown).

The first optional step is the coating of the top layer (7) with an adhesive layer (8). Coating is an open coating, so as to ensure that the top layer will keep breathability and liquid uptake properties. Coating can be carried out as porous coat, spiral-spray coating, multi lines, pattern coating, and the like. Coating methods are well known to the skilled man.

The second optional step is the spraying of adhesive for holding and/or agglomerating the particles of SAP. This spraying can be performed with an airless technique (low pressure) or air-mix. This would be applied onto the SAP particles once deposited into the pockets, substantially immediately after the SAP has been distributed from roll C4 (and before the top layer is affixed).

While the above disclosure has been given with the bottom layer receiving the SAP, it is possible, albeit less preferred, to invert the two sheet layers in the apparatus described above.

The pockets thus formed will provide for a padding or mattress feeling, which improves comfort.

When beads are present in both the MD and TD, the process disclosed above can be amended as follows. A high-speed nozzle can be arranged at the vicinity of roll C5, where the nozzle is able to deposit a band of adhesive of small width, according to the sequence of the manufacturing, usually driven by the forming roll C3. A plurality of nozzles may be needed.

Alternatively, a process known as offline process can be used. In such a situation, the bottom part of the cores are manufactured off-line (i.e. until roll C3 and C4, but before roll C5 (calendering), and then brought onto the final manufacturing line in a perpendicular manner (the final manufacturing line being the line where the absorbent article or core is inserted into a diaper for example). Beads are applied and then the top layer is applied. Calendering and cutting is then performed.

The process can be reversed, where the top layer and the bottom layers are swapped. It is also possible that pockets be formed in both layers; in such a case there will be two forming devices on the line.

The absorbent article or absorbent core of the invention can be used in a variety of products. It may be associated with a layer of fluff or cellulose layer, an acquisition/distribution layer, or both; it can also be used stacked one over the other in 2 or more layers, where the patterns of pockets may be aligned or offset, and the like, creating 3D draining network. The absorbent article or core of the invention can generally speaking be used as part of personal care products, especially diapers.

The following examples illustrate the invention without limiting it.

Example 1

Inventive Example

Test Method

Acquisition Rate Under Load

The acquisition rate test is the determination of the time that is needed for the fluid absorbent article to completely absorb a certain amount of NaCl Solution (synthetic urine) to ensure dryness even in gush situations.

For testing the acquisition rate, the absorbent article is insulted several times with defined amounts of a 0.9% NaCl solution under a load. The NaCl-solution used is a 0.9% (9 g/l) solution of sodium chloride in deionised water with a surface tension of (70±2) mN/m. The acquisition rate is measured by recording the time of the absorbent article needed for absorption of a certain amount of fluid after being maintained at a pressure of 0.7 psi for 10 min following multiple separate insults.

The acquisition rate test is carried out at a temperature of 23±2° C. and a relative humidity of 50±10%.

Materials and apparatus that are needed for carrying out the test are a 3.64 kg (±0.0075 kg) circular, 0.7 psi (±0.01 psi) weight with a diameter of 10 cm, with 2.38 cm ID Plexiglas® tube through the centre of the weight, a digital timer, an electronic balance (accuracy of 0.01 g), beakers, a ruler a separatory funnel with a flow rate at 7 g/sec±1 sec or equivalent.

The fluid absorbent article is placed flat on e.g. an Plexiglas® inspection table, e.g. by using clamps. An insult point is marked out on the article. In case of an absorbent core the point should be positioned in the centre of the core.

The 3.64 kg load is placed onto the absorbent article with the opening of the Plexiglas® tube positioned centrally on the previously marked insult point.

Defined amounts of 0.9% NaCl solution for each insult have to be chosen. Here for each insult 70 ml of the NaCl solution were used.

For the primary insult the respective amount of NaCl solution is weighed into a beaker, poured into the Plexiglas® tube and the timer is started immediately as soon as the fluid is released onto the absorbent article. The time (A1) in seconds for the fluid to be fully absorbed into the article is recorded.

After 10 minutes have elapsed, the load is removed. After 2 minutes without load, the second acquisition can be started.

The same procedure as above is repeated for the next insults.

In total 4 acquisitions are measured (each 70 ml of the NaCl solution) and the respective times A2, A3, A4 are recorded.

The acquisition rate under load is calculated according to the following equation:

Acquisition rate (g/s)=weight of NaCl solution for each insult [g]/Acquisition time for each insult [s]

Preparation of Laminates,

Inventive Example

Absorbent Article with Beads

Laminates or absorbent articles (size 30×11 cm) were prepared using a rectangular metal box of a size about 31×12 cm (slightly larger than the cores to be prepared) which was connected to a standard vacuum cleaner to create a vacuum. A plastic pattern was placed in the box. The pattern was made of a plastic plate (size 30×11 cm) in which open rectangular uniform spaces (24 spaces; each 2.0×4.0 cm) were cut. The remaining parts of the plate between the rectangular openings are about 0.5 cm wide.

A nonwoven (spunmelt PP hydrophilic nonwoven of 10 g/m$^2$ from DOUNOR—France) coated with hotmelt (Bostik, France, adhesive H4245, applied as combed slot coating 2 mm on/2 mm off with a quantity of about 5 g/m$^2$) was placed with the coated side up in the box on top of the plastic pattern. Caused by the vacuum, the nonwoven was suck into the open spaces of the pattern and pockets were created in the nonwoven. Furthermore the vacuum immobilize the nonwoven during the preparation of the laminate.

Each pocket was filled with Superabsorbent Polymer (Hysorb B 7055 from BASF (CRC=32 g/g; AUL=23 g/g)) of an amount of 0.625 g so that the core contains in total 15 grams of the fluid absorbent polymer.

Afterwards beads of hotmelt (H4245, Bostik, France) were applied to the laminate between the pockets by transferring it onto the nonwoven in the metal box by using silicon paper (stripes of the hotmelt were deposed on silicon paper and then transferred at the nonwoven) These beads (longitudinal beads, with a length of 30 cm, coating about 20 mg/m and a width of about 1 mm and latitudinal beads, with a length of 11 cm, coating about 20 mg/m, and a width of about 1 mm.) were placed between the pockets to built a "network" around the pockets.

Then a second nonwoven (spunbond PP nonwoven of 14.5 g/m$^2$ from DOUNOR—France) coated with hotmelt (Bostik adhesive H4245, applied as a full slot coating of about 5 g/m$^2$) was placed on top of the previous nonwoven with the coated side downwards. A schematically view of such a core/laminate is shown in FIG. 1a.

After the top layer was mounted on the bottom layer, the laminate was pressed using a pressure roll (weight: 2 kg, width 6 cm).

Comparative Example

Absorbent Article without Beads

The laminate or absorbent article was prepared according to the preparation of laminates with beads except the addition of beads. The second nonwoven is directly placed on top of the first one after addition of fluid-absorbent particles. The laminate was pressed using a pressure roll (weight: 2 kg, width 6 cm).

Results

Acquisition Rate Under Load:

The acquisition rate under load was measured for the comparative example laminate without beads and the inventive example of a laminate with beads for 4 insults, each of 70 ml of 0.9% NaCl solution.

The results are summarized in the following table.

TABLE 1

Results acquisition time under load

| | Acquisition time (in seconds) | | | |
|---|---|---|---|---|
| | A1 | A2 | A3 | A4 |
| Laminate without beads | 3 | 10 | 16 | 19 |
| Laminate with beads | 6 | 7 | 9 | 15 |

During the first acquisition, the liquid is quickly distributed along the channels between the pockets.

Differences can be observed starting with the second acquisition: The laminate with beads shows shorter acquisition times, since the pockets are not opened and the distribution channels can distribute the liquid even at the tertiary or fourth insult.

In case no beads are present, the pockets open. The distribution channels slowly disappear thus causing gel blocking. The liquid distribution becomes slower and the acquisition time increases.

Example 2

Inventive Example

Laminates or absorbent articles (size 30×11 cm) were prepared using the following components:

A nonwoven (spunmelt PP hydrophilic nonwoven of 10 g/m$^2$ from DOUNOR—France, unwinding tension 1 bar, winding tension 50 N) coated with hotmelt (Bostik, France, adhesive H4245, applied as combed slot coating 2 mm on/2 mm off with a quantity of about 10 g/m$^2$, spray temperature 145° C.) was used as top-sheet.

A second nonwoven (spunbond PP nonwoven of 14.5 g/m$^2$ from DOUNOR—France, drive speed 24 m/min, unwinding tension 0 bar, winding tension 50 N) was coated with hotmelt (Bostik adhesive H4245, applied as a full slot coating of about 11 g/m$^2$, spray temperature 135° C., air pressure 0.75 bar, air temperature 145° C.).

This second nonwoven was used to form the pockets on roll C3. The design used was comprising 24 pockets (rectangular uniform; each 2.0×4.0 cm). Each pocket was filled with Superabsorbent Polymer (Hysorb B 7055 from BASF [CRC=32 g/g; AUL=23 g/g]) of an amount of 0.625 g so that the core contains in total 15 grams of the fluid absorbent polymer (Settings dosing unit: SAP flow rate 58 kg/h, speed 400 rpm).

Beads of hotmelt (H4245, Bostik, France) were applied in the machine direction (MD) (in total 5 beads with a length of 30 cm, coating 0.2 g/m and a width of about 1 mm, spray temperature 135° C., melt tank temperature 135° C., adhesive pressure 24 bar).

Example of Laminate in a Diaper

Diapers dm-Babylove (Aktiv Plus, size 5 Junior, 12-25 kg; lot 140212-SE071313) were used for testing.

In order to remove the fluff-SAP core, the top-sheet of diapers was cut longitudinally (on the side along the leg-cuffs) and the acquisition layer with top-sheet were flipped aside in order to have access to the absorbing core. The fluff-core was scrapped off. The prepared laminate was placed in the position of the fluff-SAP core. The diaper was closed and the top-sheet/acquisition layers were stitched together.

Results—Acquisition Rate Under Load:

The acquisition rate under load was measured with the original dm-Babylove diaper (Aktiv Plus, size 5 Junior, 12-25 kg) as comparative example and Babylove diaper with the inventive laminate. The acquisition was measured for 4 insults, each of 70 ml of 0.9% NaCl solution.

The results are summarized in the following table 2.

TABLE 2

Results acquisition time under load

| | Acquisition time (in seconds) | | | |
|---|---|---|---|---|
| | A1 | A2 | A3 | A4 |
| Babylove diaper original | 47 | 83 | 116 | 123 |
| Babylove diaper with laminate | 34 | 34 | 23 | 25 |

The acquisition with the diaper containing the laminate is faster. The saline solution was absorbed by the laminate and no leakage was observed.

For all 4 insults the acquisition time for the original diaper is higher than for the diaper containing the inventive laminate. The diaper with laminate shows shorter acquisition times.

The invention claimed is:

1. An absorbent article (1) comprising:
    a first sheet layer (2) presenting an array of absorbent receiving pockets (4, 4a);
    masses (6) of superabsorbent material, which masses are placed in said absorbent receiving pockets (4, 4a);
    a second sheet layer (7) placed on top of the first sheet layer;
    bonding beads (5) placed between the respective pockets ensuring structural strength;
    the first sheet layer (2) forming a number of pleats (10) on the masses (6) of superabsorbent material, the pleats being present in an area that extends about the periphery of the pocket thus formed, wherein the number of pleats (10) is from 2 to 20 pleats per pocket (4, 4a), and the pleats are built substantially parallel to a plane of the first and second sheet layers,
    wherein the first sheet layer (2) is impervious to liquids and the second sheet layer (7) allows penetration of liquids into the masses of superabsorbent material.

2. The absorbent article (1) of claim 1, comprising:
    a first adhesive layer or a second adhesive layer between the first and second layers bonded in the area (9) in the vicinity of the beads (5);
    wherein the first and second adhesive layers delaminate in said area (9) upon exerting a pressure by the superabsorbent expansion.

3. The absorbent article (1) of claim 2, comprising two adhesive layers (3) and (8) applied respectively on the first and second sheet layers.

4. The absorbent article (1) of claim 1, wherein the bonding beads comprise adhesive beads in both machine and transverse directions.

5. The absorbent article (1) of claim 1, wherein the bonding beads (5) define draining zones in the part of the sheet layers in correspondence to said beads.

6. The absorbent article (1) of claim 1, wherein the bonding beads (5) are adhesive beads.

7. The absorbent article (1) of claim 1, wherein the masses of superabsorbent material further comprise an adhesive.

8. The absorbent article (1) of claim 1, wherein the first sheet layer (2) or the second sheet layer (7) is non-woven.

9. The absorbent article (1) of claim 1, wherein the first sheet layer (2) is a bottom layer and the second sheet layer (7) is a top layer.

10. The absorbent article (1) of claim 2, wherein the first and second adhesive layers and the bonding beads are non hydrosoluble.

11. The absorbent article (1) of claim 1, wherein the superabsorbent material comprises less than 30% fibers.

12. The absorbent article (1) of claim 1, wherein the superabsorbent material has a centrifuge retention capacity of at least 24 g/g.

13. The absorbent article (1) of claim 1, wherein the superabsorbent material has an absorbency under load of at least 22 g/g, the absorbency being measured under a load of 49.2 g/cm$^2$ according to EDANA test method No. WSP 242.2-05 "Absorption under Pressure".

14. The absorbent article (1) of claim 1, wherein the superabsorbent material has a saline flow conductivity of at least $25 \times 10^{-7}$ cm$^3$ s/g.

15. The absorbent article (1) of claim 1, further comprising an acquisition/distribution layer.

16. A diaper, training pant, sanitary napkin, incontinence garment or bandage comprising the absorbent article (1) of claim 1.

17. A process for the manufacture of the absorbent article (1) of claim 1, comprising the steps of:
    (1) providing a first sheet layer (2),
    (2) applying bonding beads (5) ensuring structural strength,
    (3) forming pockets (4, 4a) into said first sheet layer (2),
    (4) filling the pockets with masses of superabsorbent material, the mass of superabsorbent material (6) representing, in volume, less than 70% of the volume defined by the pockets before pleating step (7),
    (5) providing a second sheet layer (7), wherein the first sheet layer (2) is impervious to liquids and the second sheet layer (7) allows penetration of liquids into the masses of superabsorbent material,
    (6) affixing the second sheet layer (7) on the first sheet layer (2) carrying the pockets (4, 4a), and
    (7) pleating the first sheet layer (2) on the masses (6) of superabsorbent material, the pleats (10) being present in a zone that extends about the periphery of the pocket thus formed.

18. The process of claim 17, wherein the pleats (10) are formed by applying pressure in a direction that is substantially perpendicular to the plane of the layers so that the pleats (10) are built substantially parallel to the plane of the layers.

19. The process of claim 17, wherein the pleats (10) are formed from the parts of the sheets of the pockets that are perpendicular to the plane of the layers.

* * * * *